United States Patent [19]

Oesterle

[11] Patent Number: 4,577,493

[45] Date of Patent: Mar. 25, 1986

[54] DEVICE FOR PERFORMING MICROMECHANICAL MEASUREMENTS OF THE SURFACE OF TEST OBJECTS

[76] Inventor: Kurt M. Oesterle, Goldbacherstrasse 88, CH-8700 Küsnacht, Switzerland

[21] Appl. No.: 548,885

[22] PCT Filed: Jan. 6, 1983

[86] PCT No.: PCT/CH83/00001

§ 371 Date: Sep. 23, 1983

§ 102(e) Date: Sep. 23, 1983

[87] PCT Pub. No.: WO83/02666

PCT Pub. Date: Aug. 4, 1983

[30] Foreign Application Priority Data

Jan. 25, 1982 [CH] Switzerland ............... 440/82

[51] Int. Cl.$^4$ ............................................. G01N 3/42
[52] U.S. Cl. .................................................. 73/81
[58] Field of Search ............................. 73/81, 83

[56] References Cited

U.S. PATENT DOCUMENTS

| 3,877,297 | 4/1975 | Oesterle ............... 73/81 |
| 4,159,640 | 7/1979 | Leveque et al. ........ 73/81 |
| 4,245,496 | 1/1981 | Napetschnig .......... 73/83 |

FOREIGN PATENT DOCUMENTS

| 0386316 | 9/1973 | U.S.S.R. ............... 73/81 |
| 0587363 | 1/1978 | U.S.S.R. ............... 73/81 |

*Primary Examiner*—Charles A. Ruehl
*Attorney, Agent, or Firm*—Sughrue, Mion, Zinn, Macpeak and Seas

[57] ABSTRACT

The invention relates to a device for performing micromechanical measurements on the surface layer of a test object. An axially movable carrier pipe is arranged in a housing, and a measuring shaft is provided with an indentor arranged within the carrier pipe. An induction generator and an induction displacement sensor are provided surrounding the measurement shaft. A constantly increasing load is applied to the shaft, and the incremental displacement of the shaft is continually measured by the displacement sensor over a predetermined period. According to an alternative embodiment, a displacement actuation device is disposed within the carrier in order to incrementally displace the shaft, and an electrical load sensor associated with the shaft continually measures the load thereon.

18 Claims, 5 Drawing Figures

DEVICE FOR PERFORMING MICROMECHANICAL MEASUREMENTS OF THE SURFACE OF TEST OBJECTS

BACKGROUND OF THE INVENTION

The current invention refers to a device for performing micromechanical measurements on materials.

It is known that the simplest procedure for determining the behaviour and the physical constants of metallic and non-metallic materials in a micromechanical manner is to measure on the surface of a test object, the penetration depth y of a weighted indentor, such as a pyramid tip, a ball or a conical tip, while varying the force F imparted by the indentor, and to determine a characteristic of the surface layer of the test object from the quotient F/y.

In order to eliminate the inherent disadvantages of this known procedure, i.e. the dependence of the progression of the curve on the penetration depth y influenced by the force or load F and the application time, on the shape and surface consistency of the indentor, as well as, in the case of thin coatings and paint, on the layer thickness, an improved procedure for determining the infinitesimal hardness behaviour (IHV—infinitesimales Härteverhalten) has been known since 1968. In this known procedure the quotient of the force F and the penetration depth y is plotted over the force F. However, the resulting curve is also dependent on the parameters stated. However, its point of intersection with the Y-axis forms a limiting value $$IHV = \lim F/y(F) \text{ for } F \rightarrow 0,$$

which is essentially independent of parameter. This limiting value, called the IHV value, is a significant, well defined material value which is changed in a characteristic manner by the condition of and slightest changes to the material by external, often targeted, influences. Extensive tests and theoretical research have shown that the following is applicable: $IHV \sim C \sqrt{E}$, whereby C is a practically constant value for certain classes of materials and E the elastic modulus of the test object material.

In the IHV procedure, known since 1968, the registration of the value pairs F, y and of the quotients F/y, the calculation of the quotients F/y, as well as the determination of the functional dependence of the penetration depth y on the force F and of the IHV value are done essentially manually, whereby it is natural to use the usual instruments for measuring hardness. The determination of individual IHV values, and even more so the determination of a series of IHV values, take a long time.

A procedure for the determination of the infinitesimal hardness behaviour (IHV) of materials, which can be done many times faster and more accurately, is known from DE-PS No. 23 57 755. In this procedure, also known as IMD (Infinitesimal Module Determination), the surface of the test object is continuously weighted and is subject to individual weighting which changes continuously in the same manner. At time intervals the instantaneous force F and the thus attained value y of the penetration depth are determined and stored for digital registration. The stored value pairs F/y, F are processed to determine the function F/y=F/y(F), and subsequently a digital IHV value is calculated and displayed by the machine by the previously stated limit formation.

The disadvantage of all previously known methods for micromechanical measurements was that only small and very small objects, measuring, e.g. from a few millimeters to a maximum of 4 cm lateral length, could be set up for measurement in stationary machine, placed in a vibrationless manner.

SUMMARY OF THE INVENTION

It is the task of the present invention to make possible micromechanical measurements, especially according to the IHV or IMD procedure, also on large objects.

With the invention it becomes possible to execute micromechanical measurements without the need of a small surface test object. IHV or IMD measurements of the type known from DE-PS No. 23 57 755 may be directly performed on large objects such as machines, vehicles, facades etc. in a rapid and reliable manner.

Instead of aiming for the desired precision in the usual manner by using smaller and smaller weight weighting objects, it is possible with the current invention to use large measuring units which register well and accurately to automatically determine the regularity of the process of infinitesimalization and—to determine based on this—the stated IHV or IMD limiting values of the respective material. This process makes it possible—without difficulty—to separate the measuring device into two main components, namely a mobile measuring head which finally produces technical measuring values, and a separate stationary electronic processing system, which is connected to the measuring head.

BRIEF DESCRIPTION OF THE DRAWINGS

Various embodiments of the subject invention will be explained below, in conjunction with the following drawing in which.

DETAILED DESCRIPTION OF THE PREFERRED EMBODIMENTS

Figure 1:
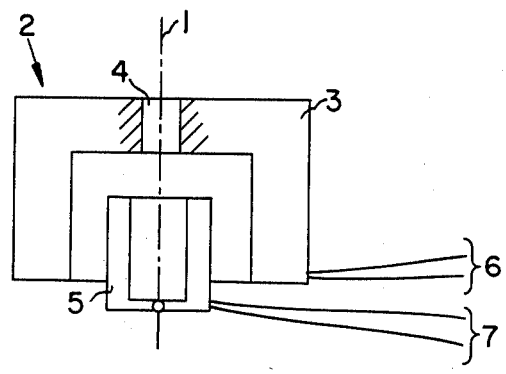
FIG. 1 is a schematic representation of an inductive generator or power source for use in the measuring head of the device according to the invention.

In FIG. 1, a measuring shaft 1 of the present measuring head—further described in connection with FIGS. 4 and 5—is schematically represented. The measuring shaft 1 has—on the end designed to act on the surface layer of the test object—an indentor, which is not shown. To exert a lengthwise force on the measuring shaft 1—and therefore onto the indentor—the induction generator 2, shown schematically in FIG. 1, has a solenoid or a permanent magnet 3 in a pot shape which is mounted to the housing of the measuring head—not shown in FIG. 1—and has an opening 4 to allow passage of the measuring shaft 1. On the inside of the pot is another solenoid 5 which is firmly connected to the measuring shaft 1. Through feeder cables 6, the solenoid 3 is provided with constant power (naturally these feeder lines are omitted if a permanent magnet is used instead of a solenoid). Other supply cables 7, which lead to a physically separate control device, provide the second solenoid 5 with controlled adjustable direct current. By suitable adjustment of this direct current in the control device it is possible to exert a variable force on the lengthwise freely moving measuring shaft 1 in the housing of the measuring head. This induction generator can also be used as induction provider.

Figure 2:
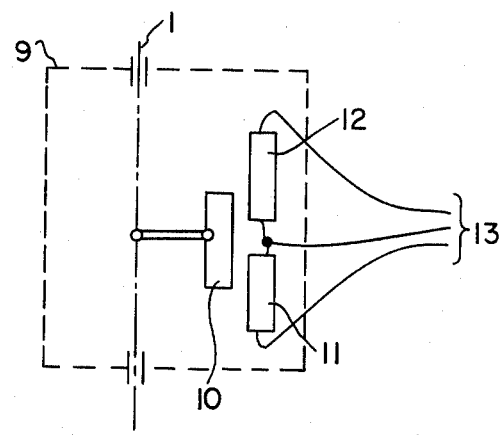
FIG. 2 is a schematic representation of an inductive displacement sensor for use in the measuring head of the device according to the invention.

Shown in FIG. 2 is an induction displacement sensor 9 which registers a lengthwise movement of the measuring shaft 1, i.e. the incremental penetration depth into the surface layer of the test object by the indentor attached to the measuring shaft 1. For this purpose a magnetic core or rotor 10 is firmly connected to the measuring shaft 1. Adjacent a rotor 10, two lengthwise arranged solenoids 11 and 12 are provided, which are mounted in a stationary manner relative to the measuring shaft 1. Solenoids 11, 12 form elements of an external separate measuring bridge (not shown), with which they are connected by cables 13. A lengthwise shift of the measuring shaft 1 has the effect—because of the changed position of the rotor 10 relative to the solenoids 11, 12—of detuning the measuring bridge and thus creating an electrically measurable indication of the shifting of the measuring shaft 1 and therefore the indentor.

Instead of the induction measuring device 9, it would be possible to use a piezoelectric element as a displacement sensor.

Figure 3:
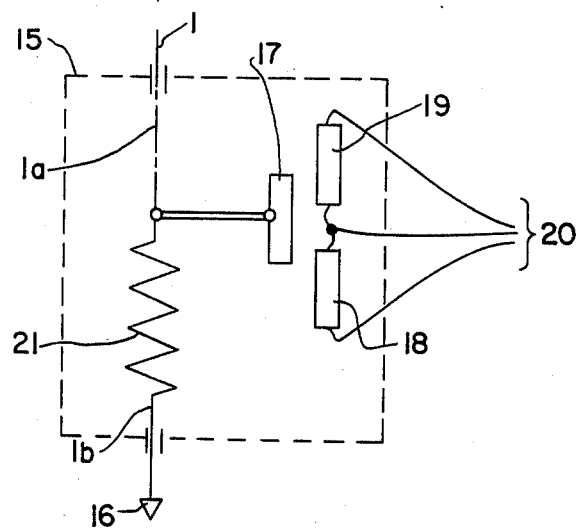
FIG. 3 is a schematic representation of an inductive force transducer for use in the measuring head of the device according to the invention.

FIG. 3 shows, schematically, an inductive force transducer 15, with which the force is registered which—during a lengthwise shift of the measuring shaft 1—is exerted by the attached indentor 16 on the surface layer of the test object. The force transducer 15 also contains a rotor 17 which is firmly connected to the measuring shaft 1, for which, again, two lengthwise arranged solenoids 18 and 19 of an external measuring bridge—connected through cables 20—are provided. Between a section 1a of the measuring shaft 1, to which the rotor is attached, and a section 1b of the measuring shaft 1, which carries the indentor, there is a spring 21. By the force exerted by the measuring shaft 1—or rather the segment 1a—the spring 21 is compressed, which causes the rotor 17 to be displaced with respect to the solenoids 18, 19 of the measuring bridge. The degree of detuning of the measuring bridge is therefore a measure for the force exerted by the indentor 16 onto the surface layer of the test object.

Figure 4:
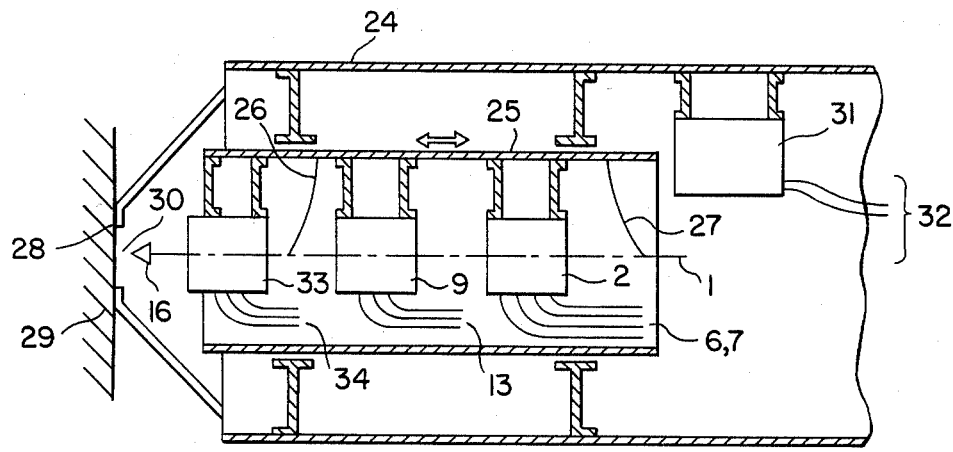
FIG. 4 is a schematic representation of a first example of a measuring head for registration of the penetration depth depending on the penetration force at a constant measuring time.
Figure 5:
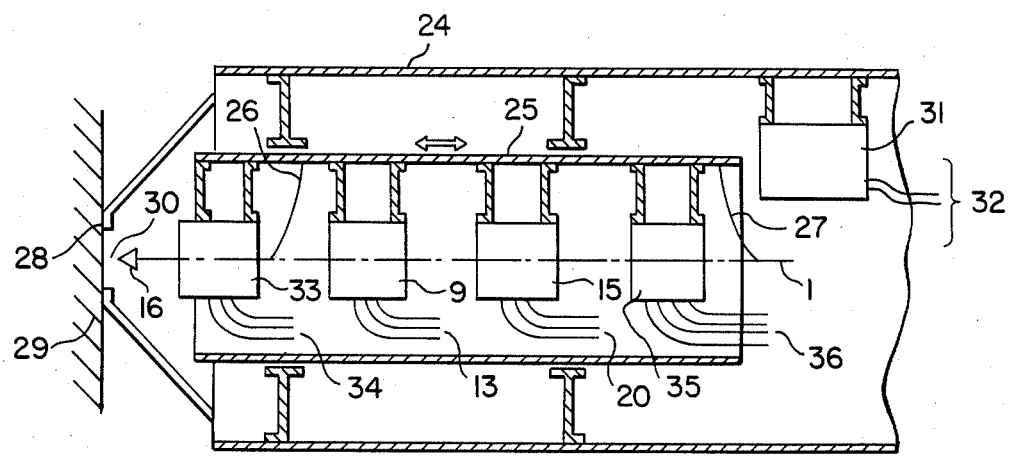
FIG. 5 is a schematic representation of a second example of a measuring head for the registration of the penetration force depending on the penetration depth at a constant measuring time.

Shown in FIGS. 4 and 5 are examples of the measuring head which selectively uses the measuring elements described in FIGS. 1 to 3. All the schematically shown measuring heads have an elongated housing or casing 24, which can be hand held, in which an axially moveable carrier pipe 25 is arranged. In this carrier pipe 25, the measuring shaft 1 is positioned with the use of an astatic pair of springs 26, 27, or possibly with several such pairs of springs, in such a manner that the measuring shaft 1 can move lengthwise through the bearings without exerting force. On the front side, the housing 24 has a contact surface 28, formed by three support pods, which permit the positioning and pressing of the measuring head against the surface of the test object 29. Between the support pods of the contact surface 28 there is an opening 30, which permits the indentor 16—which is attached to the end of the measuring shaft 1—to pass in order to act on the surface layer of the test object 29. In all examples shown, the carrier pipe 25 is connected to a stepping motor 31, attached to the housing 24, at the end removed from the one carrying the indentor 16, to which control impulses are led from an external separate control device through cables 32 and which effects a foreward and backward movement of the carrier pipe 25, and with it, the measuring shaft 1. In addition, each of the measuring heads of FIGS. 4 and 5 has an inductive zero indicator 33 on the end of the carrier pipe 25 near the indentor, which can be designed according to the displacement sensor of FIG. 2 and has a corresponding electrical connection 34. The zero indicator 33 has the task of indicating, by an electrical signal, each time the tip of the indentor 16 is at least approximately in the plane of the contact surface 28 or rather touches the surface of the test object when the measuring head is applied.

The electrical connecting cables shown in FIGS. 4 and 5 are led together, e.g. as a multi-wire cable, to a separate central and stationary control and processing device, the construction of which is not the subject of this invention.

In the model according to FIG. 4, there are positioned in the carrier pipe 25 and in working connection to the measuring shaft 1, an induction generator 2—according to the example in FIG. 1—and an inductive displacement sensor 9—according to the example in FIG. 2. After the measuring head has been set on the test object 29, the stepping motor 31 effects—through the carrier pipe 25—a coarse advance movement of the measuring shaft 1 until the zero indicator 33 reacts when the tip of the indentor 16 is at least near the plane of the contact surface 28 of the housing 24, or rather, when it touches the surface of the test object 29, at which moment the stepping motor is shut off.

At this point the induction generator 2 is switched on, which now—subject to the value F of the respective force—incrementally displaces the measuring shaft 1 and effects the penetration of the indentor 16 into the surface layer of the test object 29. The corresponding penetration depth y is in each case determined by the induction displacement sensor 9 and passed as an electrical signal to the cables 13.

After a certain penetration depth y has been reached, the power generator 2 is switched off and the stepping motor 31 is reset to return the measuring shaft 1 to its original position. The establishment of the curve $y = f(F)$ for constant time intervals and the determination of the IHV or IMD value takes place in the central control and processing installation.

It is also possible—however relatively unsuitable because of a lower degree of precision—to use a suitable measuring head for registering the dependence of the penetration depth y with time at a constant force F, instead of the dependence of the penetration depth y on force F for a constant time or time interval, as it is done with the measuring head according to FIG. 4.

For this measuring procedure the measuring head has—in working connection with the measuring shaft 1—an induction power generator 2 and an induction displacement sensor 9, as was already shown in the model in FIG. 4. However, here the power generator 2 is made and controlled in such a way that the power supply remains constant, independent of the actually very small displacement of the measuring shaft 1.

The nullification by the stepping motor 31 and the zero indicator 33 are done in the same manner as in the model in FIG. 4. After the stepping motor 31 is shut off, the induction generator 2 is turned on to exert a constant force onto the measuring shaft 1 and through it onto the indentor 16. During this constant force application the induction sensor 9 registers the penetration depth y of the indentor 16 into the surface layer of the test object 29, in dependence on the penetration time, and passes corresponding signals to the cables 13. When a prescribed penetration depth has been reached, the induction generator 2 is switched off and the stepping motor 31 turned on to return the measuring shaft 1 to its original position.

The control and processing device transforms the y values and time values which were registered at constant force F, into corresponding relationships with a straight time axis for increased precision, and determines from this the IHV value in a known manner.

In the model according to FIG. 5, a power source 35 with connecting cables 36 is arranged in working connection with the measuring shaft 1 inside the carrier pipe 25. Unit 35 can be another stepping motor or may be constructed as an induction power source like the power generator 2 in FIG. 1. In addition, an inductive force transducer 15 is installed—in working connection to the measuring shaft 1—in the carrier pipe 25. Device 15 is as described, e.g., in FIG. 3. As the spring 21 in FIG. 3 is installed between the segment of the measuring shaft 1 which is influenced by the power source 35—designated as 1a in FIG. 3—and the segment of the measuring shaft 1—designated as 1b in FIG. 3—which carries the indentor 16, there is a displacement sensor 9 in working connection with the measuring shaft 1, which may be constructed, e.g., according to FIG. 2 installed in the carrier pipe 25.

With the illustrated measuring head, together with the previously mentioned central control and processing device, the following measuring procedure is executed: The measuring head is—with its contact surface 28—set on the test object 29. Then, the stepping motor 31 is turned on. The stepping motor 31 then pushes the measuring shaft 1 with the indentor 16 relatively rapidly forward through the carrier pipe 25 until the zero indicator 33 indicates by a certain signal that the tip of the indentor is at least near the plane of the contact surface 28, or rather touches the surface of the test object 29 (zero or reference position of the measuring shaft 1).

At that point, the stepping motor 31 is shut off and the power source 35 turned on in order to advance the measuring shaft 1 in incremental steps. The inductive force transducer 15 registers the penetration force F in dependence on the penetration depth y caused by the power source 35 and measured by the displacement sensor 9 and outputs continuous or incremental corresponding signals to the cables 20, which are processed in the central control and processing device according to the curve y=f(F) for constant time intervals.

Only after a certain penetration depth y has been reached, the stepping motor 31 is turned off and then switched on in reverse in order to return the measuring shaft 1 to its original position. The processing of the signals passed by the measuring head to the central control and processing device, including storage, takes place in this device, for example in the manner known from DE-PS No. 23 57 755 to determine the already mentioned IHV or IMD values.

In measurements with the described measuring heads, the actual force F imparted by the indentor 16 is—depending on the material of the test object—in the range of several 10 mN to several N, while the penetration depths are in the range of about 0.2 to 100 $\mu$m.

The illustrated arrangement of the axially moveable carrier pipe 25, propelled by the stepping motor 31, in which the measuring shaft 1 and all the power sources and sensors are located, has the effect that the coarse forward movements of the measuring elements and the measuring shaft have no influence on the measured values. That is, the measured values furnished by the measuring elements do not contain the coarse displacement required to reach a reference position of the measuring shaft. By the arrangement of the carrier pipe 25 with the stepping motor 31 it is also possible to attain compensation for the earth speed-up. Even though the described measuring head is held by hand against the surface of the test object during the whole measuring procedure, there are—during practical usage—no discrepancies which cause errors in the measurement results, because the three-point support of the measuring head on the surface of the test object precludes undefined contact, and also because the measuring procedure is of relatively short duration, some 10 to 60 seconds. Also possible deviations in individual values can be averaged out by electronic processing, especially in the formation of parameter values. If desired, the housing 24 of the measuring head can be provided with means which hold the measuring head firmly, but removably, in a vertical or almost vertical position when it is sitting on the surface of the test object, for example a flexible suction device, an adhesive layer or the like.

I claim:

1. A measuring head for use in a micro-mechanical materials measurement system, comprising; a housing having a longitudinal axis, a contact surface at one end of said housing for positioning said housing on surface layer of a test object, said contact surface being substantially perpendicular to said axis and having an opening therein about said axis, a measuring shaft disposed within said housing for displacement along said axis, said shaft being provided with an indentor at its end adjacent to said contact surface of said housing, said opening in said contact surface permitting the passage of said indentor beyond said contact surface, an electrically controllable load actuation device disposed within said housing and associated with said measuring shaft, for exerting a continually incrementally varying load on said measuring shaft in a direction along said axis toward said contact surface of said housing, a control parameter of said actuation device being related to the amount of load exerted on said measuring shaft, and an electrical displacement sensor disposed within said housing and associated with said measuring shaft for continually measuring incremental displacements thereof, said actuation device and said displacement sensor being provided with electrical cable means for remote connection to an electronic control and processing device.

2. A measuring head for use in a micromechanical materials measurement system, comprising; a housing having a longitudinal axis, a contact surface at one end of said housing for positioning said housing on a surface layer of a test object, said contact surface being substantially perpendicular to said axis and having an opening therein about said axis, a measuring shaft disposed within said housing for displacement along said axis, said shaft being provided with an indentor at its end adjacent to said contact surface of said housing, said opening in said contact surface permitting the passage of said indentor beyond said contact surface, an electrically controllable load actuation device disposed within said housing and associated with said measuring shaft for exerting a constantly increasing load on said measuring shaft in a direction along said axis toward said contact surface of said housing, a control parameter of said actuation device being related to the amount of load exerted on said measuring shaft, and an electrical displacement sensor disposed within said housing and associated with said measuring shaft for continually measuring incremental displacements thereof over a predetermined period, said actuation device and said displacement sensor being provided with electrical cable means for remote connection to an electronic control and processing device.

3. A measuring head for use in a micromechanical materials measurement system, comprising; a housing having a longitudinal axis, a contact surface at one end of said housing for positioning said housing on a surface layer of a test object, said contact surface being substantially perpendicular to said axis and having an opening therein about said axis, a measuring shaft disposed within said housing for displacement along said axis, said shaft being provided with an indentor at its end adjacent to said contact surface of said housing, said opening in said contact surface permitting the passage of said indentor beyond said contact surface, an electrically controllable displacement actuation device disposed within said housing and associated with said measuring shaft for displacing said measuring shaft along said axis towards said contact surface of said housing, and an electrical load sensor disposed within said housing and associated with said measuring shaft for continually measuring the load on said measuring shaft, said displacement actuation device and said load sensor being provided with electrical cable means for remote connection to an electronic control and processing device.

4. The measuring head as claimed in any of claims 1, 2 or 3, further including measuring shaft mounting means comprising at least one pair of astatic springs for enabling said measuring shaft to move in a longitudinal direction substantially without any force being exerted by said at least one pair of springs in said direction.

5. The measuring head as claimed in any of claims 1, 2 or 3, further including a stepping motor mounted within said housing and operatively connected to said measuring shaft in a manner so as to longitudinally displace said measuring shaft at least to a reference position at which a longitudinal extremity of said indentor lies substantially in the plane of said contact surface of said housing.

6. The measuring head as claimed in claim 5, further comprising an inductive electrical zero indicator mounted within said housing for generating an electrical signal when said indentor of said measuring shaft has attained said reference position.

7. The measuring head as claimed in claim 6, wherein said zero indicator comprises a magnetic armature firmly connected to said measuring shaft, and a stationary solenoid arrangement associated with said magnetic armature.

8. The measuring head as claimed in any of claims 1 or 2, comprising a tubular carrier mounted within said housing for movement in the direction of said longitudinal axis of said housing, a stepping motor connected to said tubular carrier; said measuring shaft, said load actuation device, said displacement sensor and a measuring shaft position zero indicator being disposed within said tubular carrier and connected thereto.

9. The measuring head as claimed in claim 8 wherein said electrically controllable load actuation device includes a two-part inductive device, one of said inductive parts being firmly connected to said measuring shaft and the other being connected to said tubular carrier, at least one of said inductive parts comprising a solenoid.

10. The measuring head as claimed in claim 8 wherein said electrical displacement sensor comprises an inductive device and includes a magnetic armature firmly connected to said measuring shaft, and solenoid means for said magnetic armature, said solenoid means being connected to said tubular carrier.

11. The measuring head as claimed in one of claims 1 or 2 wherein said electrically controllable load actuation device includes a two-part inductive device, one of said inductive parts being firmly connected to said measuring shaft and the other being connected to said housing, at least one of said inductive parts comprising a solenoid.

12. The measuring head as claimed in one of claims 1 or 2 wherein said electrical displacement sensor comprises an inductive device and includes a magnetic armature firmly connected to said measuring shaft, and solenoid means for said magnetic armature, said solenoid means being connected to said housing.

13. The measuring head as claimed in claim 3, comprising a tubular carrier mounted within said housing for movement in the direction of said longitudinal axis of said housing, a stepping motor connected to said tubular carrier, and said measuring shaft, said displacement actuation device, said load sensor and a measuring shaft position zero indicator being disposed within said tubular carrier and connected thereto.

14. The measuring head as claimed in claim 13, wherein said electrically controllable displacement actuation device includes a two-part inductive device, a first of said inductive parts being firmly connected to said measuring shaft and the other being connected to said tubular carrier, at least one of said inductive parts comprising a solenoid.

15. The measuring head as claimed in claim 13, wherein said electrical load sensor is an inductive device and includes a magnetic armature firmly connected to said measuring shaft, a compression spring disposed between said magnetic armature and said indentor, and solenoid means for said magnetic armature, said solenoid means being firmly connected to said tubular carrier.

16. The measuring head as claimed in claim 3, wherein said electrically controllable displacement actuation device includes a stepping motor.

17. The measuring head as claimed in claim 3, wherein said electrically controllable displacement actuation device includes a two-part inductive device, a first of said inductive parts being firmly connected to said measuring shaft and the other being connected to said housing, at least one of said inductive parts comprising a solenoid.

18. The measuring head as claimed in claim 3, wherein said electrical load sensor is an inductive device and includes a magnetic armature firmly connected to said measuring shaft, a compression spring disposed between said magnetic armature and said indentor, and solenoid means for said magnetic armature, said solenoid means being firmly connected to said housing.

* * * * *